US012706182B2

(12) United States Patent
Melkote

(10) Patent No.: US 12,706,182 B2
(45) Date of Patent: Aug. 11, 2026

(54) METHOD AND SYSTEM OF GENERATING, DELIVERING AND DISPLAYING CROSS PLATFORM PERSONALIZED DIGITAL SOFTWARE APPLICATIONS

(71) Applicant: Ramaswamy N. Melkote, Los Altos, CA (US)

(72) Inventor: Ramaswamy N. Melkote, Los Altos, CA (US)

( * ) Notice: Subject to any disclaimer, the term of this patent is extended or adjusted under 35 U.S.C. 154(b) by 121 days.

(21) Appl. No.: 17/705,387

(22) Filed: Mar. 28, 2022

(65) Prior Publication Data

US 2022/0375549 A1 Nov. 24, 2022

Related U.S. Application Data

(63) Continuation-in-part of application No. 17/485,484, filed on Sep. 26, 2021, now abandoned.

(51) Int. Cl.

| | |
|---|---|
| ***G16H 10/20*** | (2018.01) |
| ***G06F 3/04847*** | (2022.01) |
| ***G06F 3/0486*** | (2013.01) |
| ***H04L 51/02*** | (2022.01) |

(52) U.S. Cl.
CPC ......... *G16H 10/20* (2018.01); *G06F 3/04847* (2013.01); *G06F 3/0486* (2013.01); *H04L 51/02* (2013.01)

(58) Field of Classification Search
CPC .... G16H 10/20; G16H 40/20; G06F 3/04847; G06F 3/0486; G06F 8/35; G06F 8/34; H04L 51/02
See application file for complete search history.

(56) References Cited

U.S. PATENT DOCUMENTS

| | | | | |
|---|---|---|---|---|
| 10,943,407 | B1 * | 3/2021 | Morgan | G16H 15/00 |
| 2019/0073197 | A1 * | 3/2019 | Collins | G06F 8/60 |
| 2020/0203008 | A1 * | 6/2020 | Hawkins | G16H 40/63 |
| 2021/0228276 | A1 * | 7/2021 | Giraldez | G09B 1/00 |

* cited by examiner

*Primary Examiner* — Chinyere Mpamugo

(57) ABSTRACT

In one aspect, a computerized method for generating a personalized digital software application comprising: providing an application modeler engine. With the application modeler engine the method provides a graphical display of a palate that comprises a list all the nodes that are available to include in an application definition file(s). The application modeler engine receives a set of nodes via a drag and drop operation into the application definition file. The application modeler engine defines and integrates a chatbot into the personalized digital software application. The application modeler engine automatically creates the application definition file to run on a mobile device of the patient, wherein the application definition file follows a protocol and logic created in the application by a care team and the drag and dropped nodes. The application modeler engine uses the application definition file to generate the application from the application definition file. The application modeler engine deploys the application to a user's mobile device.

14 Claims, 19 Drawing Sheets

300

300

FIGURE 4
REPORT
MODULE CREATOR
RULES
CONTENT
Parameters
Scheduling
Select interval:
Add daily start time:
Enter number of days:
daily
Display

400

Type 2 diabetes (T2D), formerly known as adult-onset diabetes, is a form of diabetes that is characterized by high blood sugar, insulin resistance, and relative lack of insulin.

Common symptoms include increased thirst, frequent urination, and unexplained weight loss Symptoms may also include increased hunger, feeling tired, and sores that do not heal. Often symptoms come on slowly. Long-term complications from high blood sugar include heart disease, strokes, diabetic retinopathy which can result in blindness, kidney failure, and poor blood flow in the limbs which may lead to amputations. The sudden onset of hyperosmolar hyperglycemic state may occur; however, ketoacidosis is uncommon.

Next

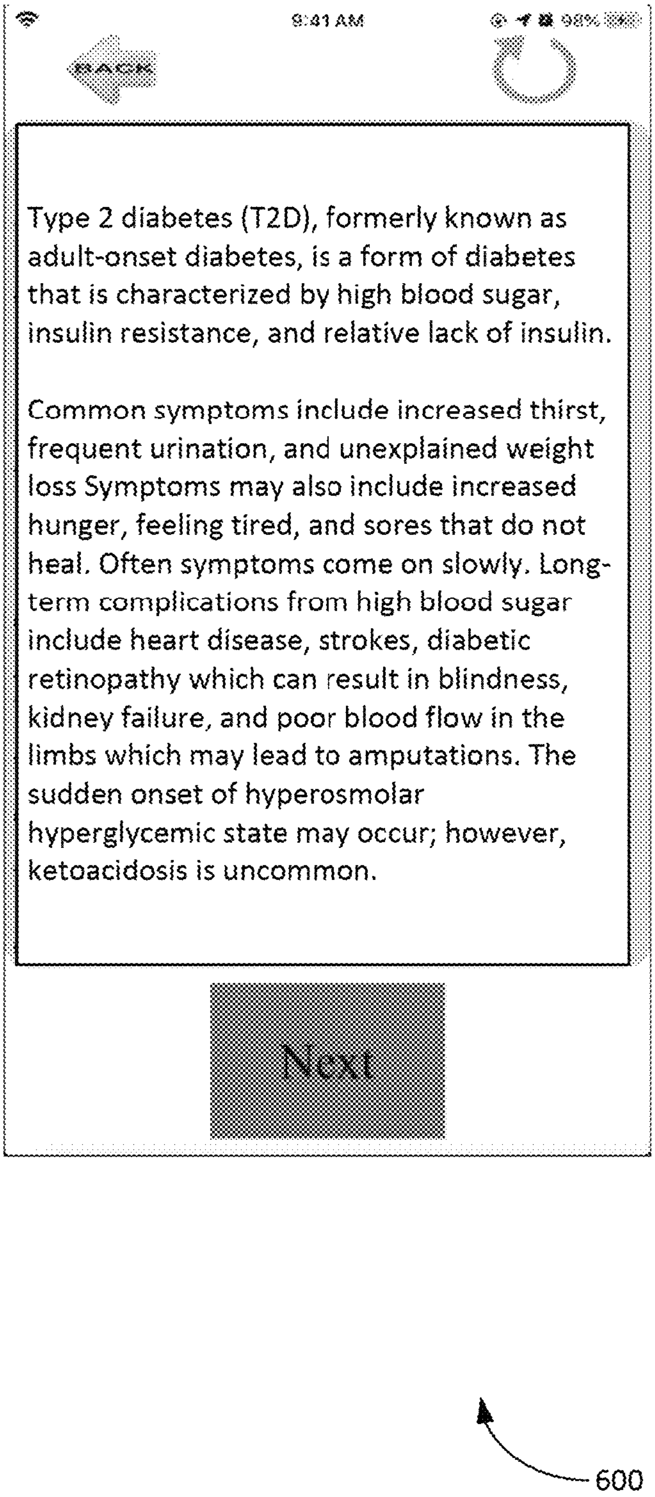

Rule Editor

Rule Condition Palette Section

Choose Variable

Enter Number 0.0 Enter

Rule Attributes Section id: 6

Rule Description:

Patient has no redness in the gums and no ulcers or fungus in the foot.

Rule Conditional: ~(REDNESS | ULCERS)

Result: G

Validate Save

1600

METHOD AND SYSTEM OF GENERATING, DELIVERING AND DISPLAYING CROSS PLATFORM PERSONALIZED DIGITAL SOFTWARE APPLICATIONS

CLAIM OF PRIORITY

This application claims priority to and is a continuation in part of U.S. patent application Ser. No. 17/485,484, titled METHOD AND SYSTEM OF GENERATING, DELIVERING AND DISPLAYING CROSS PLATFORM PERSONALIZED DIGITAL SOFTWARE APPLICATIONS and filed on 26 Sep. 2021. This application is incorporated herein by reference in its entirety.

U.S. patent application Ser. No. 17/485,484 claims priority to U.S. Provisional Application No. 63/056,714, filed on Jul. 27, 2020. This application is incorporated herein by reference in its entirety.

This application claims priority to and is a continuation in part of U.S. patent application Ser. No. 15/484,153, titled METHOD AND SYSTEM OF GENERATING, DELIVERING AND DISPLAYING CROSS PLATFORM PERSONALIZED DIGITAL SOFTWARE APPLICATIONS and filed on Apr. 11, 2017. This application is incorporated herein by reference in its entirety.

FIELD OF INVENTION

This invention related to machine learning for optimizing application development, and more specifically for generating, delivering, and displaying cross platform personalized digital software applications.

BACKGROUND

The immediate need for a patient engagement solution is one of post discharge. Readmission occurs as patients and caregivers do not understand discharge instructions. They do not adhere to the regimen and there is poor and untimely communication about patient's progress or lack of back to the physician. On the longer term, there is a need for technology aids to help combat onset of diseases.

The current products that try and address this market have significant gaps. They have boiler plate applications with heavy need for Logic/UI/Content customization for physicians and patients. This is very important as there is considerable variation in the regimen standardization amongst physicians. The customizations are either left to the practice or the patient and need extensive software coding effort. Further, there is an overhead to roll out the customized applications on both the Android and iPhone platforms. Lastly, there is no support for co-morbidity as many patients need more than one app.

Improvements to machine learning for optimizing application development, and more specifically for generating, delivering, and displaying cross platform personalized digital software applications are desired.

SUMMARY OF THE INVENTION

In one aspect, a computerized method for generating a personalized digital software application comprising: providing an application modeler engine. With the application modeler engine the method provides a graphical display of a palate that comprises a list all the nodes that are available to include in an application definition file(s). The application modeler engine receives a set of nodes via a drag and drop operation into the application definition file. The application modeler engine defines and integrates a chatbot into the personalized digital software application. The application modeler engine automatically creates the application definition file to run on a mobile device of the patient, wherein the application definition file follows a protocol and logic created in the application by a care team and the drag and dropped nodes. The application modeler engine uses the application definition file to generate the application from the application definition file. The application modeler engine deploys the application to a user's mobile device.

BRIEF DESCRIPTION OF THE DRAWINGS

The present application can be best understood by reference to the following description taken in conjunction with the accompanying figures, in which like parts may be referred to by like numerals.

FIG. 6 shows a display of textual information for the query, according to some embodiments.

Figure 9:
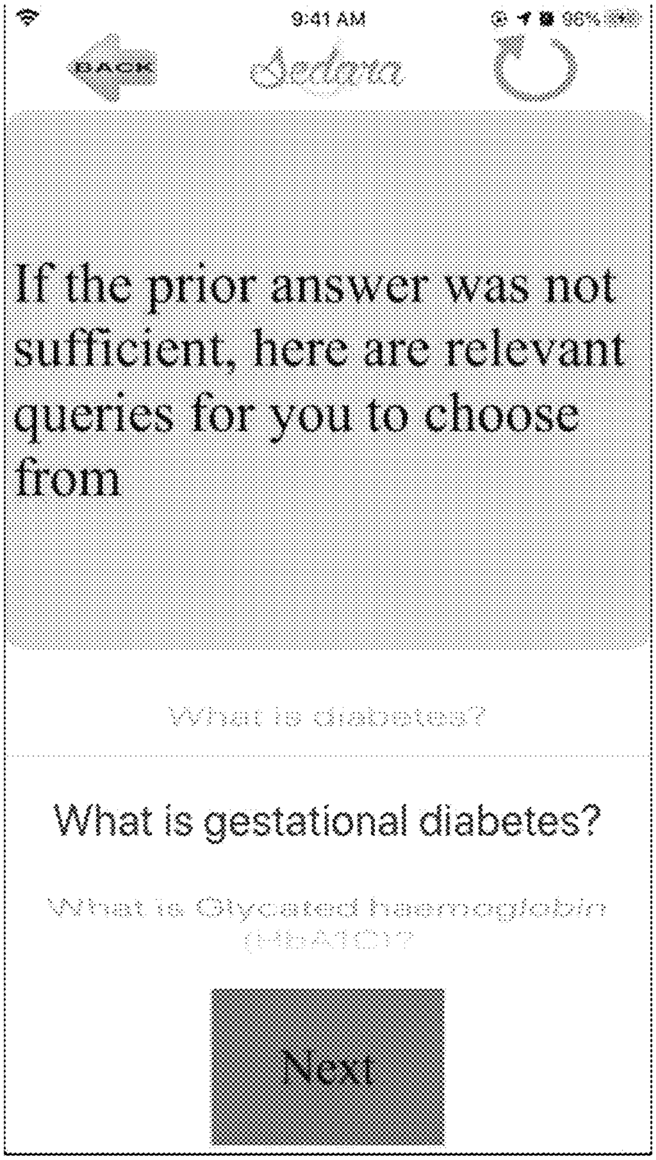

If the answers are not satisfactory to the patient, the system suggests related queries for the patient as shown in FIG. 9, according to some embodiments.

Figure 10:
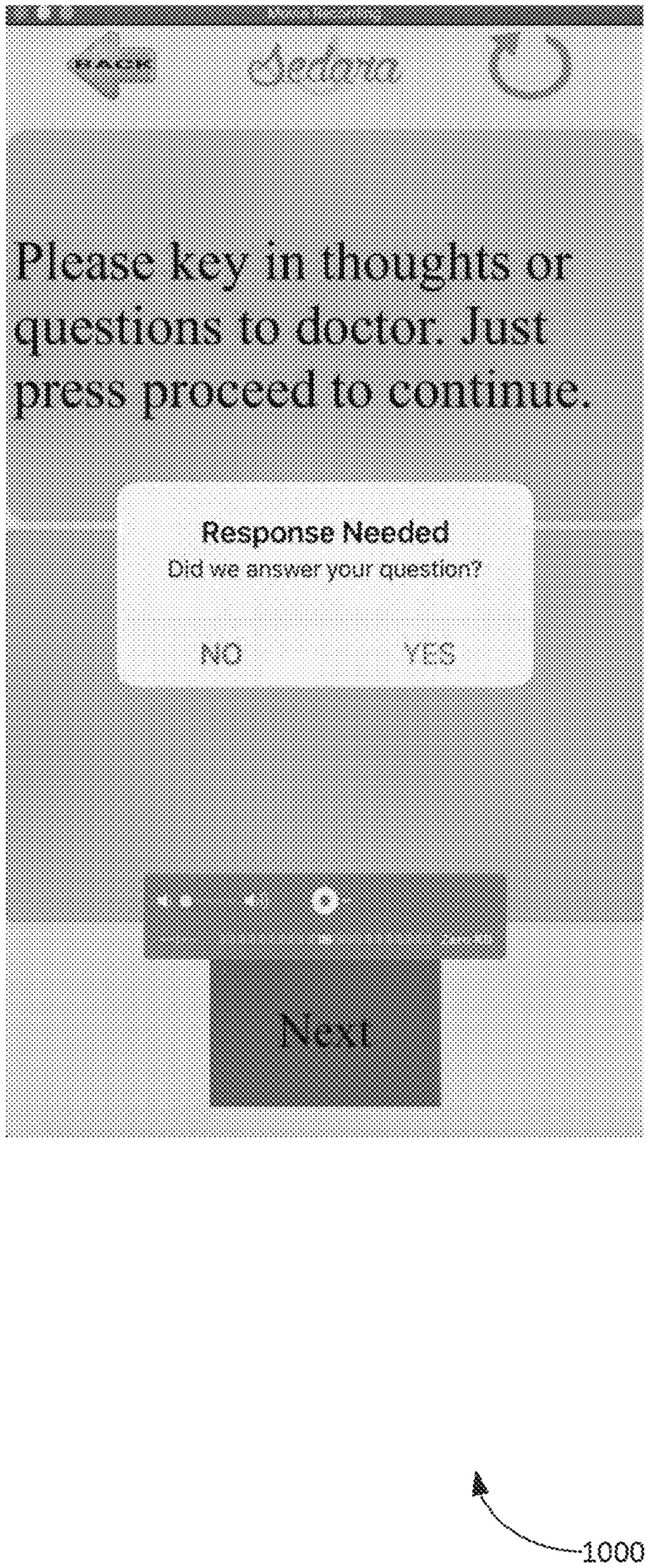

If the answers are not satisfactory to the patient, the system relays the question to the care team to answer it for the patient as shown in FIG. 10, according to some embodiments.

FIGS. 11-16 illustrate additional screen shots for implementing various embodiments.

Figure 17:
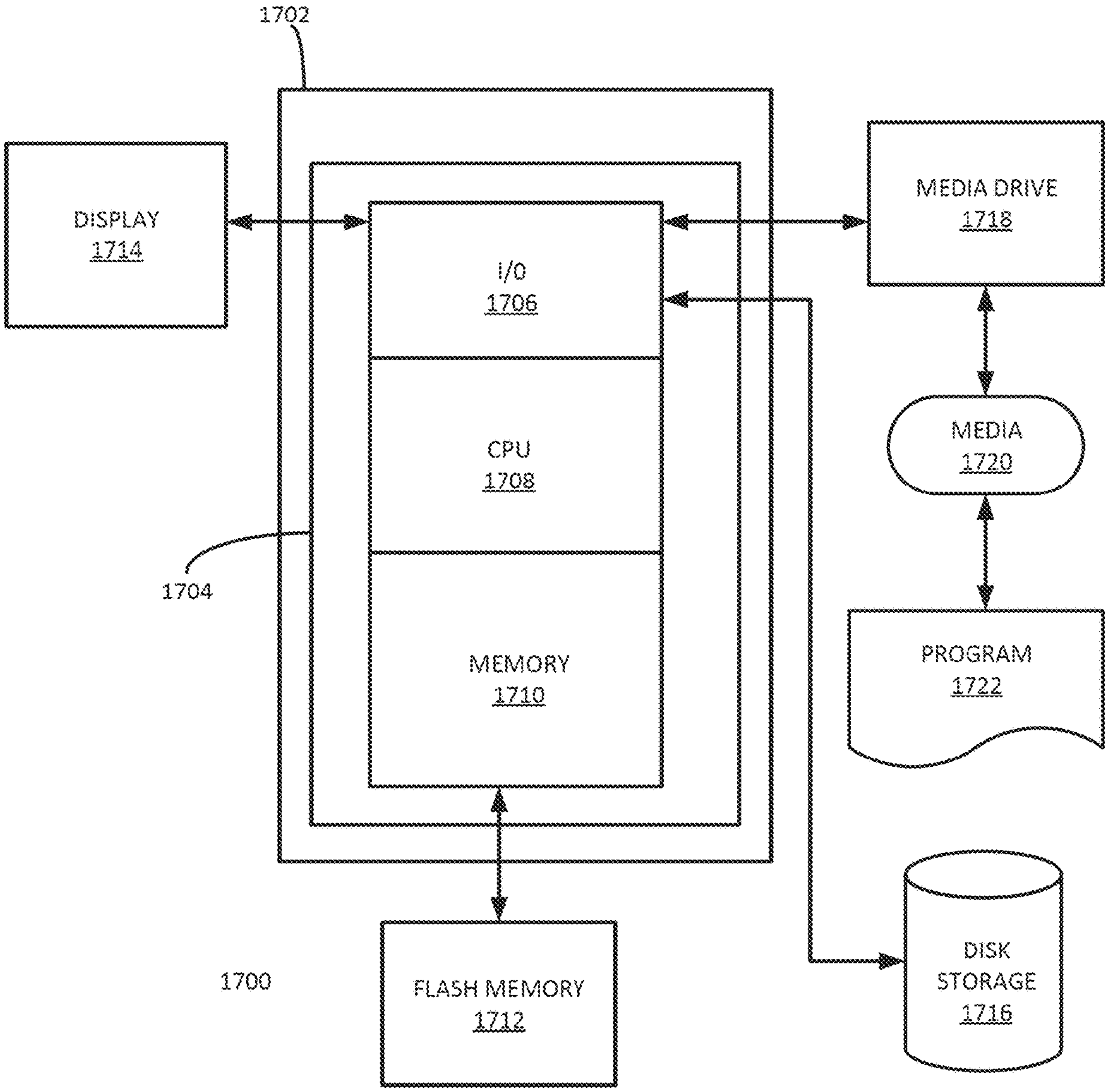

FIG. 17 depicts an exemplary computing system that can be configured to perform any one of the processes provided herein.

Figure 18:
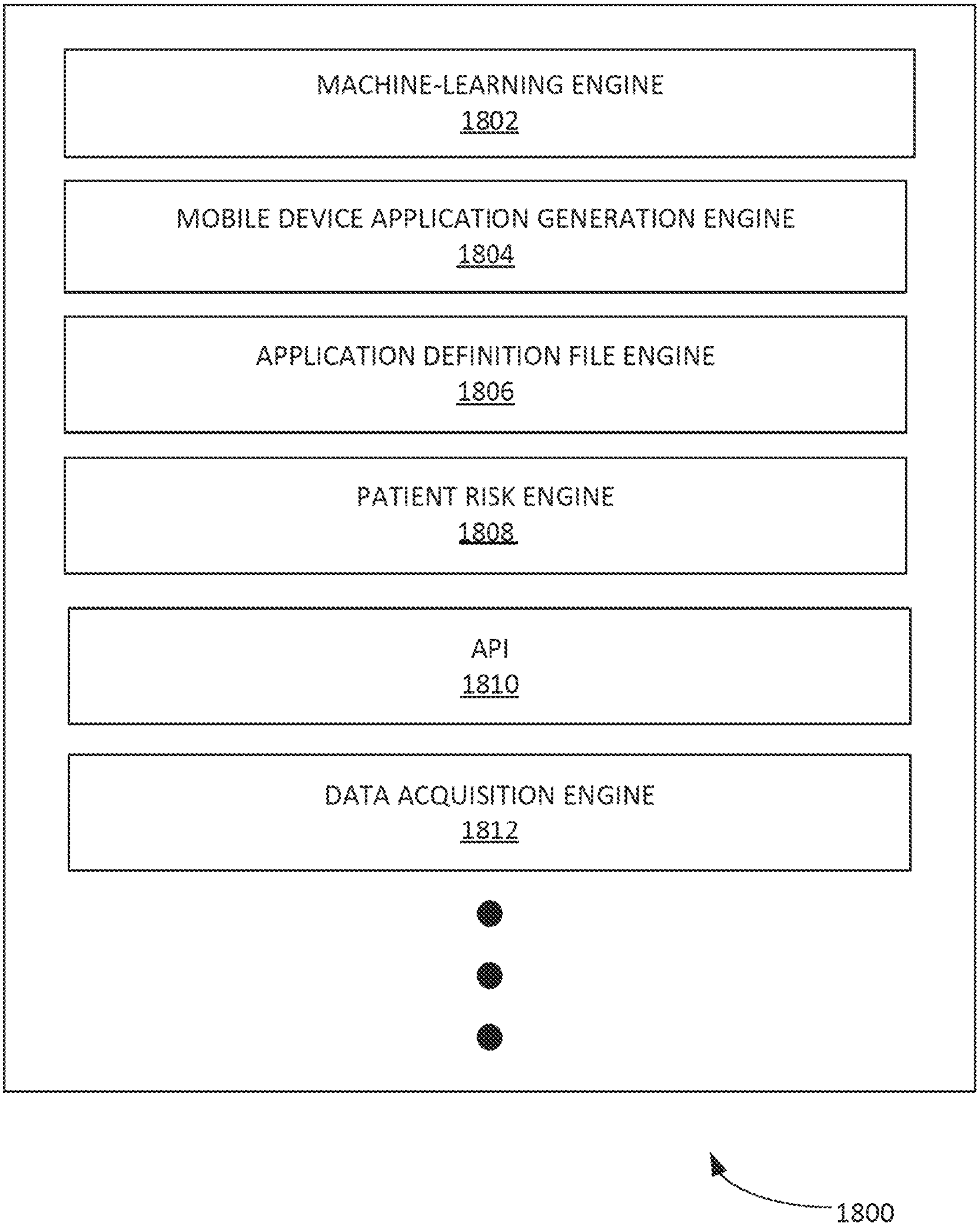

FIG. 18 illustrates an example system for generating, delivering, and displaying cross platform personalized digital software applications, according to some embodiments.

Figure 19:
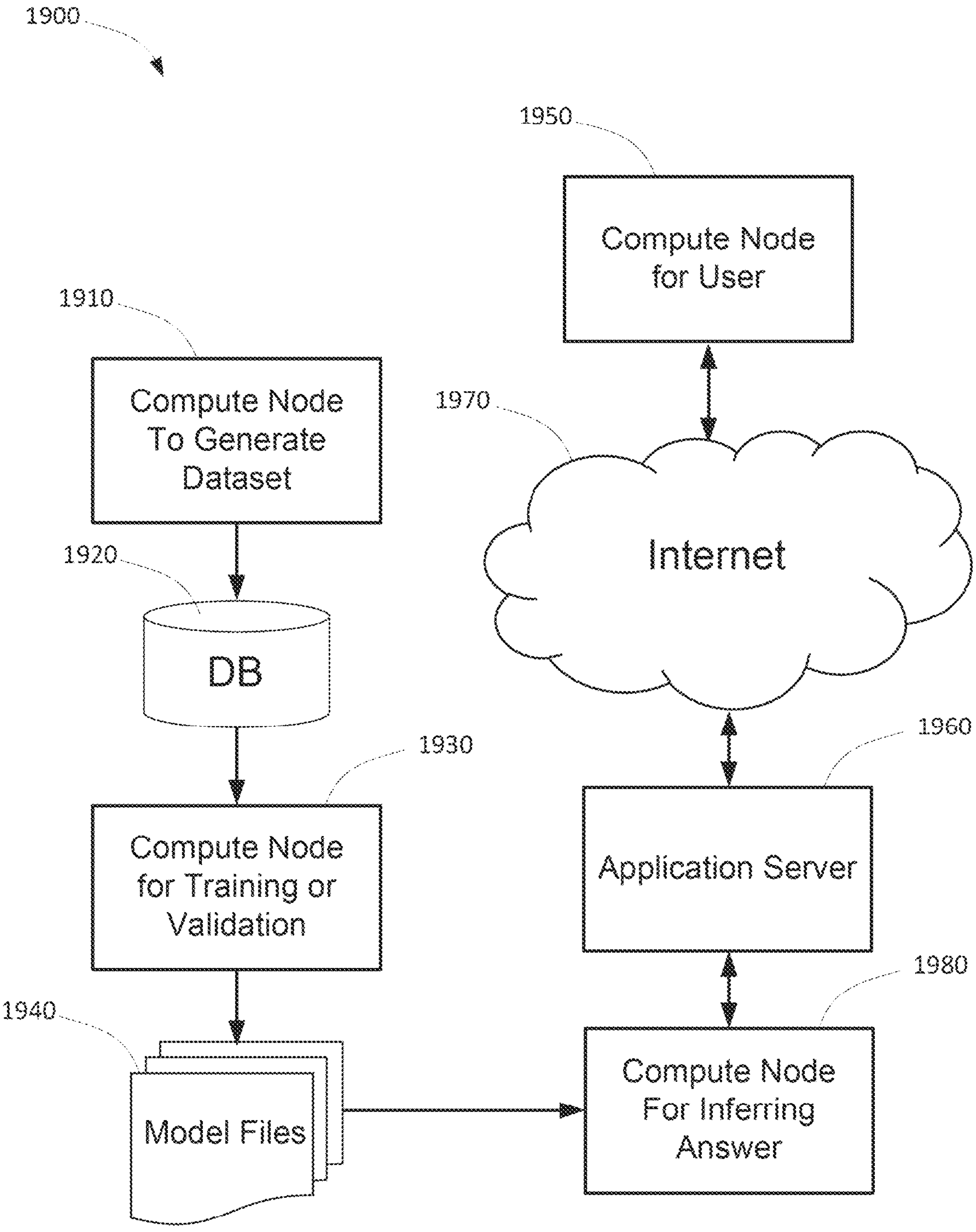

FIG. 19 illustrates a schematic representation of an exemplary hardware environment for generation of datasets for machine learning models used to determine a personalized digital software application, according to some embodiments.

The Figures described above are a representative set and are not an exhaustive with respect to embodying the invention.

DESCRIPTION

Disclosed are a system, method, and article of manufacture for generating, delivering, and displaying cross platform personalized digital software applications. The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments.

Reference throughout this specification to "one embodiment," "an embodiment," "one example," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art can recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, and they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Definitions

App store (or application marketplace) is a type of digital distribution platform for computer software called applications, often in a mobile context. applications (i.e. mobile-device applications, etc.) can provide a specific set of functions which, by definition, do not include the running of the computer itself. Complex software designed for use on a personal computer, for example, may have a related application designed for use on a mobile device. applications can be designed (e.g. by the application design systems discussed infra like system 1800, etc.) to run on a specific operating system (e.g. contemporary iOS, macOS, Windows, Android, etc.), as well as mobile carriers with proprietary portals for applications and related media content.

Apple Healthkit can include a health informatics mobile application . This can include an application programming interface (API) included in the iOS SDK (Software Development Kit). It can be used by software developers to design applications that have extensibility and that can interact with the health application on iOS.

Bluetooth is a wireless technology standard used for exchanging data between fixed and mobile devices over short distances using short-wavelength UHF radio waves in the industrial, scientific, and medical radio bands, from 2.402 GHz to 2.480 GHz, and building personal area networks (PANS).

Chatbot is a software application used to conduct an on-line chat conversation via text or text-to-speech, in lieu of providing direct contact with a live human agent. Chatbots can be used in dialog systems for various purposes including customer service, request routing, or for information gathering. While some chatbot applications use extensive word-classification processes, Natural Language processors, and sophisticated AI, others simply scan for general keywords and generate responses common phrases obtained from an associated library or database.

Drag and drop is a pointing device gesture in which the user selects a virtual object by "grabbing" it and dragging it to a different location or onto another virtual object. In general, it can be used to invoke many kinds of actions, or create various types of associations between two abstract objects.

Expert system is a computer system that emulates the decision-making ability of a human expert. Expert systems can be designed to solve complex problems by reasoning through bodies of knowledge, represented mainly as if—then rules rather than through conventional procedural code.

Google Fit is a health-tracking platform developed by Google for the Android operating system, Wear OS, and Apple Inc.'s IOS. It can include a single set of APIs that blends data from multiple applications and devices. Google Fit uses sensors in a user's activity tracker or mobile device to record physical fitness activities (e.g. walking, cycling, etc.), which are measured against the user's fitness goals to provide a comprehensive view of their fitness.

Machine learning (ML) can use statistical techniques to give computers the ability to learn and progressively improve performance on a specific task with data, without being explicitly programmed. Deep learning is a family of machine learning methods based on learning data representations. Learning can be supervised, semi-supervised or unsupervised. Machine learning is a type of artificial intelligence (AI) that provides computers with the ability to learn without being explicitly programmed. Machine learning focuses on the development of computer programs that can teach themselves to grow and change when exposed to new data. Example machine learning techniques that can be used herein include, inter alia: decision tree learning, association rule learning, artificial neural networks, inductive logic programming, support vector machines, clustering, Bayesian networks, reinforcement learning, representation learning, similarity, and metric learning, and/or sparse dictionary learning.

Machine learning is a type of artificial intelligence (AI) that provides computers with the ability to learn without being explicitly programmed. Machine learning focuses on the development of computer programs that can teach themselves to grow and change when exposed to new data. Example machine learning techniques that can be used herein include, inter alia: decision tree learning, association rule learning, artificial neural networks, inductive logic programming, support vector machines, clustering, Bayesian networks, reinforcement learning, representation learning, similarity, and metric learning, and/or sparse dictionary learning. Random forests (RF) (e.g. random decision forests) are an ensemble learning method for classification, regression, and other tasks, that operate by constructing a multitude of decision trees at training time and outputting the class that is the mode of the classes (e.g. classification) or mean prediction (e.g. regression) of the individual trees. RFs can correct for decision trees' habit of overfitting to their training set. Deep learning is a family of machine learning methods based on learning data representations. Learning can be supervised, semi-supervised or unsupervised.

Natural-language generation (NLG) is a software process that produces natural language output. NLG can include, inter alia: content determination (e.g. deciding what information to mention in the text); document structuring (e.g. overall organization of the information to convey); aggregation (e.g. merging of similar sentences to improve readability and naturalness); lexical choice (putting words to the concepts); referring expression generation (e.g. creating referring expressions that identify objects and regions); and realization (creating the actual text, which should be correct according to the rules of syntax, morphology, and orthography; etc.

Natural language processing (NLP) is a subfield of linguistics, computer science, information engineering, and artificial intelligence that manages the interactions between computers and natural languages. NLP systems can include, inter alia: speech recognition systems, natural language understanding systems, optical character recognition systems and natural language generation systems. NLP includes methods to analyze large amounts of natural language data. ML systems discussed herein can utilize NLP methods for developing training and verification data sets. ML systems can also use NLP methods to analyze and optimize specified user input.

Predictive Analytics includes the finding of patterns from data using mathematical models that predict future outcomes. Predictive analytics encompasses a variety of statistical techniques from data mining, predictive modelling, and machine learning, that analyze current and historical facts to make predictions about future or otherwise unknown events. In business, predictive models exploit patterns found in historical and transactional data to identify risks and opportunities. Models can capture relationships among many factors to allow assessment of risk or potential associated with a particular set of conditions, guiding decision-making for candidate transactions.

EXAMPLE METHODS

Example methods can be used to customize and deploy built application modules for Android/iPhones that can be utilized by patients and caregivers. Example methods can provide fully native application with complete access to Bluetooth Devices (e.g. BP, weight etc.). These can be native Android/iPhone application that run the application module that takes the patient through the regimen. Example methods can be used to create educational content for patients. It is noted that the same native application can be deployed to Android/iPhone/iPad instantly with consistent experience. The applications can automatically obtain the health information from Apple Healthkit on iPhone and Google Fit on Android. The records of patient interactions can be obtained and sent to a server-side system (e.g. system 1800 discussed infra, etc.). The methods can use predictive analytics/machine learning. In this way, methods can spot trends to proactively stop readmissions, etc. Various detailed and summary reports that flag patient risk stratification (e.g. RYG, etc.) conditions of patients with alerts sent out to care team. Methods provided herein can be used to support for co-morbidity. Additionally, multiple applications can be deployed to the same patient device and run seamlessly as single applications. The methods herein can use a drag and drop application modeler to create applications and rules for an expert system in minutes. An automated application model and rules verification to ensure quality of applications. The methods can leverage a chatbot to answer questions for various conditions.

Example methods can address the gaps discussed supra efficiently. With the example platform, example methods can build applications that are customized to physician, patient, and condition. With a drag and drop modeler, example methods can create applications to a practice's specification in minutes without coding. This lets us offer all customizations as a service. Example methods can configure applications fast not months of custom software work that the competing products entail. The same application can be deployed as fully native applications on iPhone® and Android®. The application can be fully native with access to all low-level device functionality and peripheral integrations. Multiple applications can be deployed to the same patient to support co-morbidity and run seamlessly as one application. This is the major differentiation for our product given that majority of acute cases suffer from more than one condition.

Figure 1:
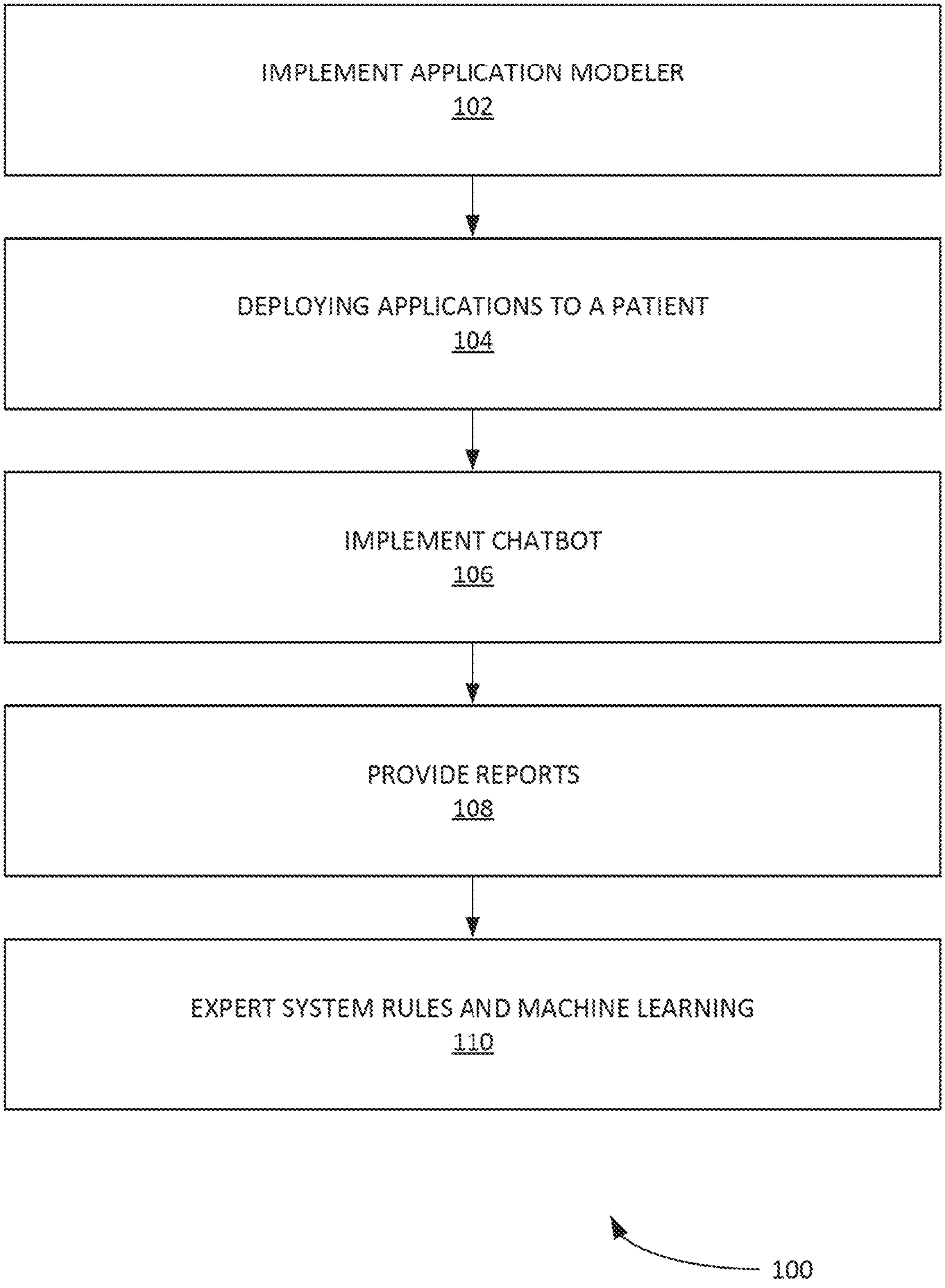
FIG. 1 illustrates an example process for generating, delivering, and displaying cross platform personalized digital software applications, according to some embodiments.

FIG. 1 illustrates an example process 100 for generating, delivering, and displaying cross platform personalized digital software applications, according to some embodiments.

Figure 2:
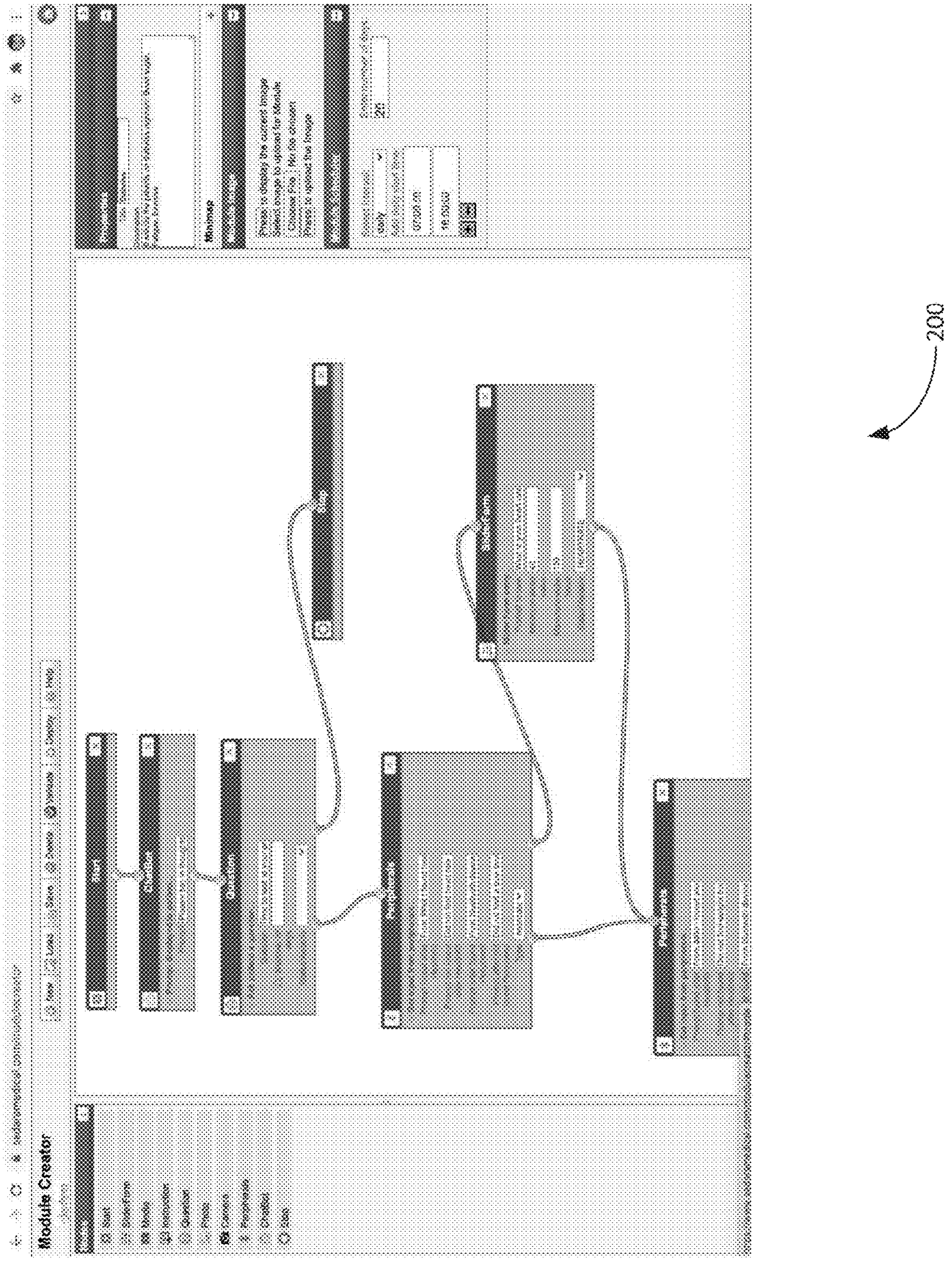
FIG. 2 illustrates an example screen shot of an interface for creating an application definition file with a drag and drop application modeler, according to some embodiments.

In step 102, process 100 can create the application definition file with a drag and drop application modeler such as one shown in FIG. 2. More specifically, there can be a palate that could contain all the nodes that are available. The list can contain the following among others:

start: where the application starts;

stop: where the application stops;

slider form: for providing data input in a range like pain rating from 1 to 10;

digital media: for displaying audio and video content locally from the mobile phone or via the internet;

instruction: for displaying instructions to the patient;

question: for asking Yes/No questions to the patient or multi-list selection list for soliciting input from patients;

photo: for displaying photos that are generic educational photos or photos specific to the patient digital camera: for enabling patients can take photographs of their injuries etc.

peripherals: can include data that is obtained from peripheral devices that are connected to the mobile phone via protocols like Bluetooth etc. (e.g. heartrate, BP, blood sugar, weight, temperature etc.);

chatbot: can include which the patients can use to ask questions to educate themselves on their condition.

The application created by the modeler creates the application definition file that when runs on the mobile phone of the patient can follow the protocol and logic created in the application by the care team. The application can, at this stage, pass the baton to the care team as they ask questions and interact with the patient. The chatbot passes the baton to patient where the patient can ask free form questions to the application.

In the center pane of FIG. 2 are the nodes which are selected, dragged, and dropped from the palate on the left.

The nodes are wired together again by drag and drop. The result is a graph that is saved as the application definition file. Each node has customizable parameters to tailor the information for the specific application as shown in FIG. 2. For example, for a slider form, the customizable parameters are, inter alia:

Prompt displayed to the user;

Minimum slider value;

Maximum slider value; and

Tag phrase that tags the data.

On the right pane in FIG. 2 are properties of the application and the default schedule for the application. The schedule specifies the time intervals in which the application starts on the patient device (e.g. daily, every other day, every week, at 8:00 AM, 3:00 PM, 8:00 PM, etc.). It also specifies for how long the application will run on the patient device.

Figure 3:
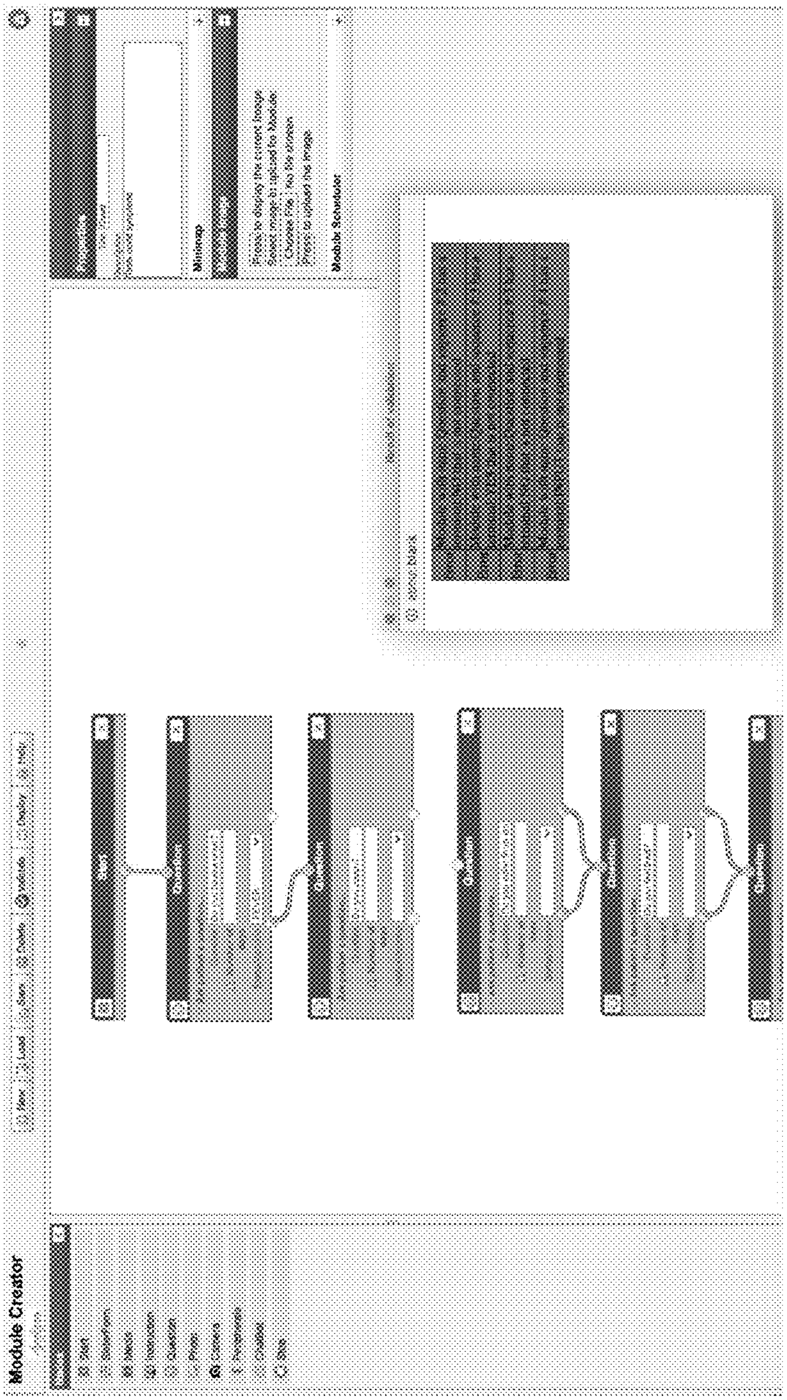
FIG. 3 illustrates an example interface for the user to validate and/or compile a created application, according to some embodiments.

FIG. 3 illustrates an example interface 300 for the user to validate and/or compile a created application, according to some embodiments. The compilation/validation errors are displayed to the user that the user can correct, save, and deploy the application and make it ready for serving to patients. The modeler enables the user to, inter alia:

customize and deploy built application modules to Android/iPhones for Patients and caregivers;

deploy fully native application with complete access to Bluetooth Devices (BP, weight etc.);

native android/iPhone applications run the application module that takes the patient through the regimen;

create educational content for patients;

same native application deployed to Android/iPhone/iPad instantly with consistent experience;

the instructions in the application definition file could be modified based on patient feedback; and the application definition file on a patient device can be updated by sending a SMS message or push notification to the device.

Figure 4:
FIG. 4 illustrates an example interface for deploying applications to a patient, according to some embodiments.

In step 104, process 100 can deploy the applications to a patient. FIG. 4 illustrates an example interface for deploying applications to a patient, according to some embodiments. FIG. 4 illustrates that for an example comorbid patient, "Ram Melkote", three applications have been deployed, including, inter alia:

would-care;

behavioral health;

diabetes; etc.

As shown, each application can have customizable parameters for that particular patient. Also, the schedule for application activation on the patient device can be created specifically for the patient in context, that overrides the default schedule created in the modeler as shown in FIG. 2.

Figure 5:
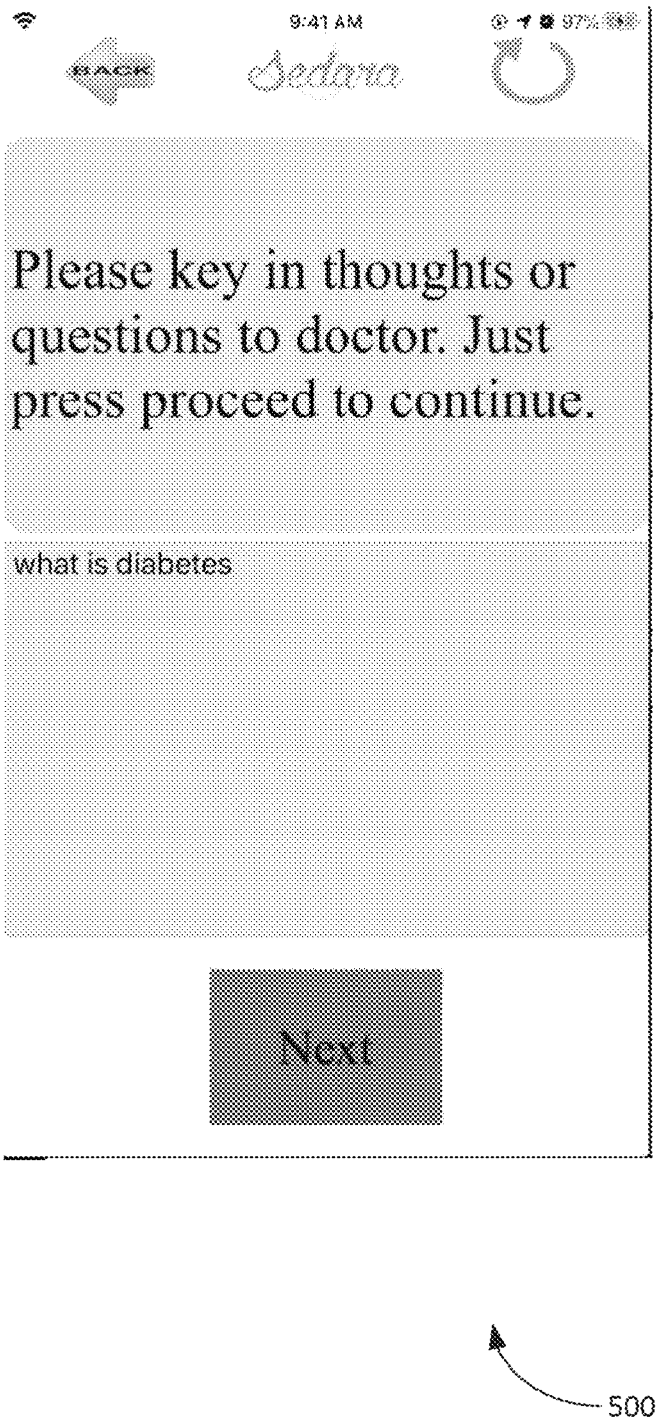
In FIG. 5, the patient keys in a query: "what is diabetes", according to some embodiments.
Figure 7:
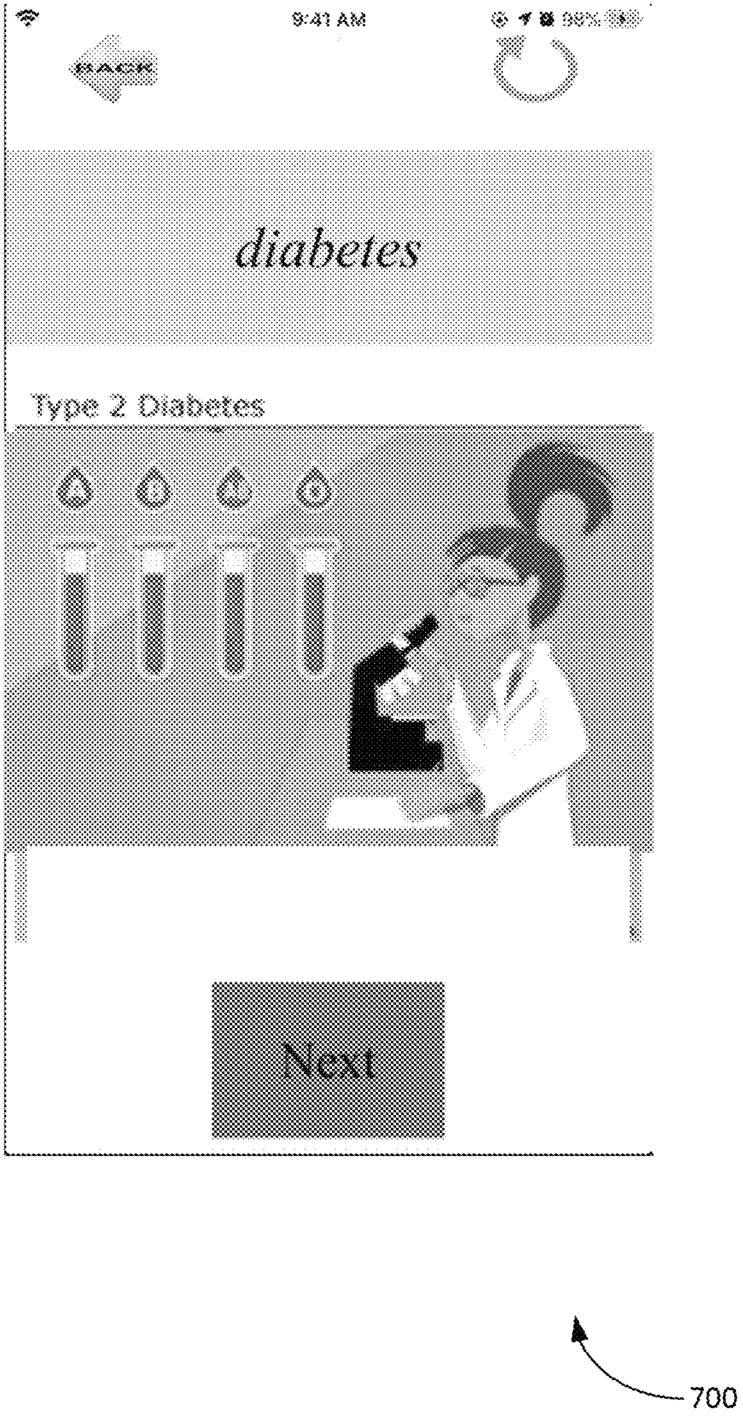
FIG. 7 illustrates displaying image-based information for the query, according to some embodiments.
Figure 8:
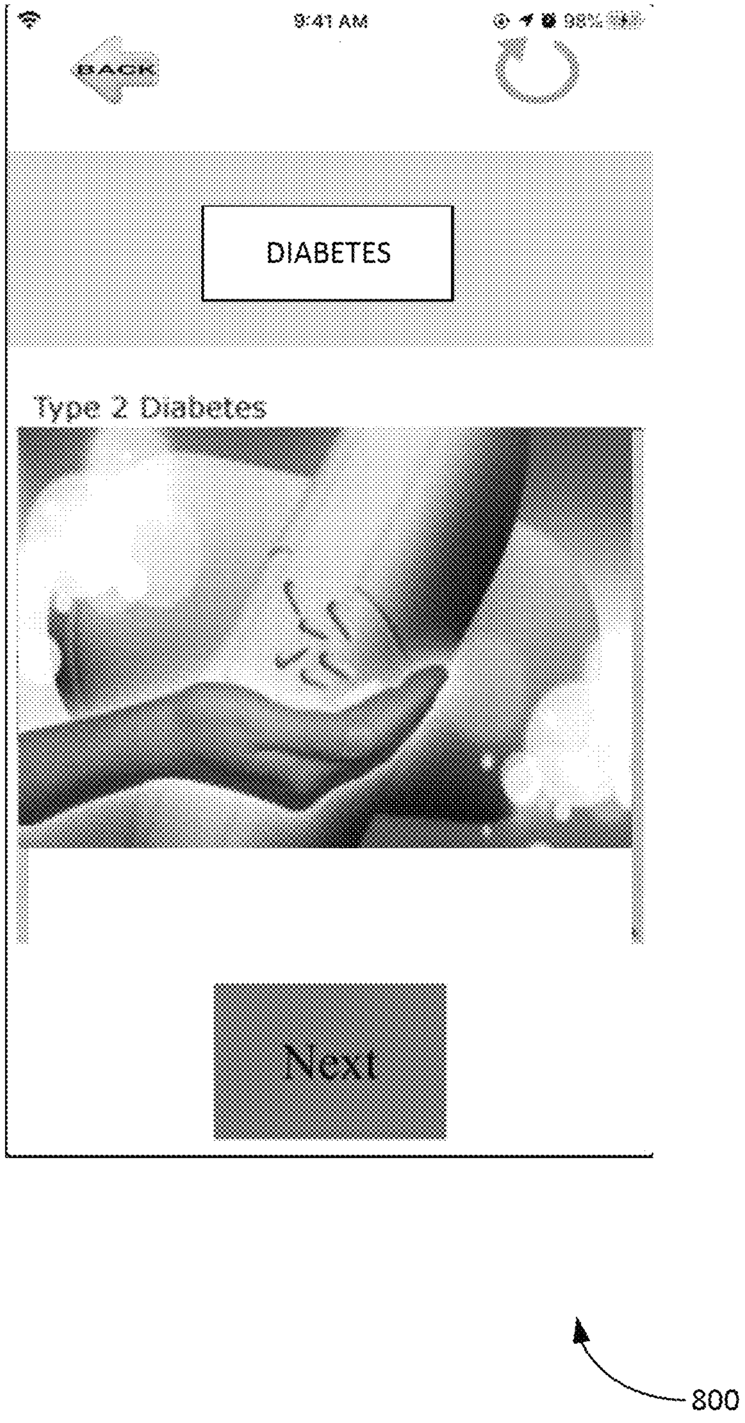
FIG. 8 illustrates displaying video-based information for the query, according to some embodiments.

In step 106, process 100 can implement a chatbot. The chatbot can be enable patients to ask questions to educate themselves on their condition. As a result, process 100 uses an NLP engine that analyzes the query, and replies with a multi-media answer to the patient. FIGS. 5-10 illustrate example screen shots for implementing a chatbot functionality, according to some embodiments. In FIG. 5, the patient keys in a query: "what is diabetes". FIG. 6 shows a display of textual information for the query. FIG. 7 illustrates displaying image-based information for the query. FIG. 8 illustrates displaying video-based information for the query. If the answers are not satisfactory to the patient, the system suggests related queries for the patient as shown in FIG. 9. If the answers are not satisfactory to the patient, the system relays the question to the care team to answer it for the patient as shown in FIG. 10.

Figure 11:
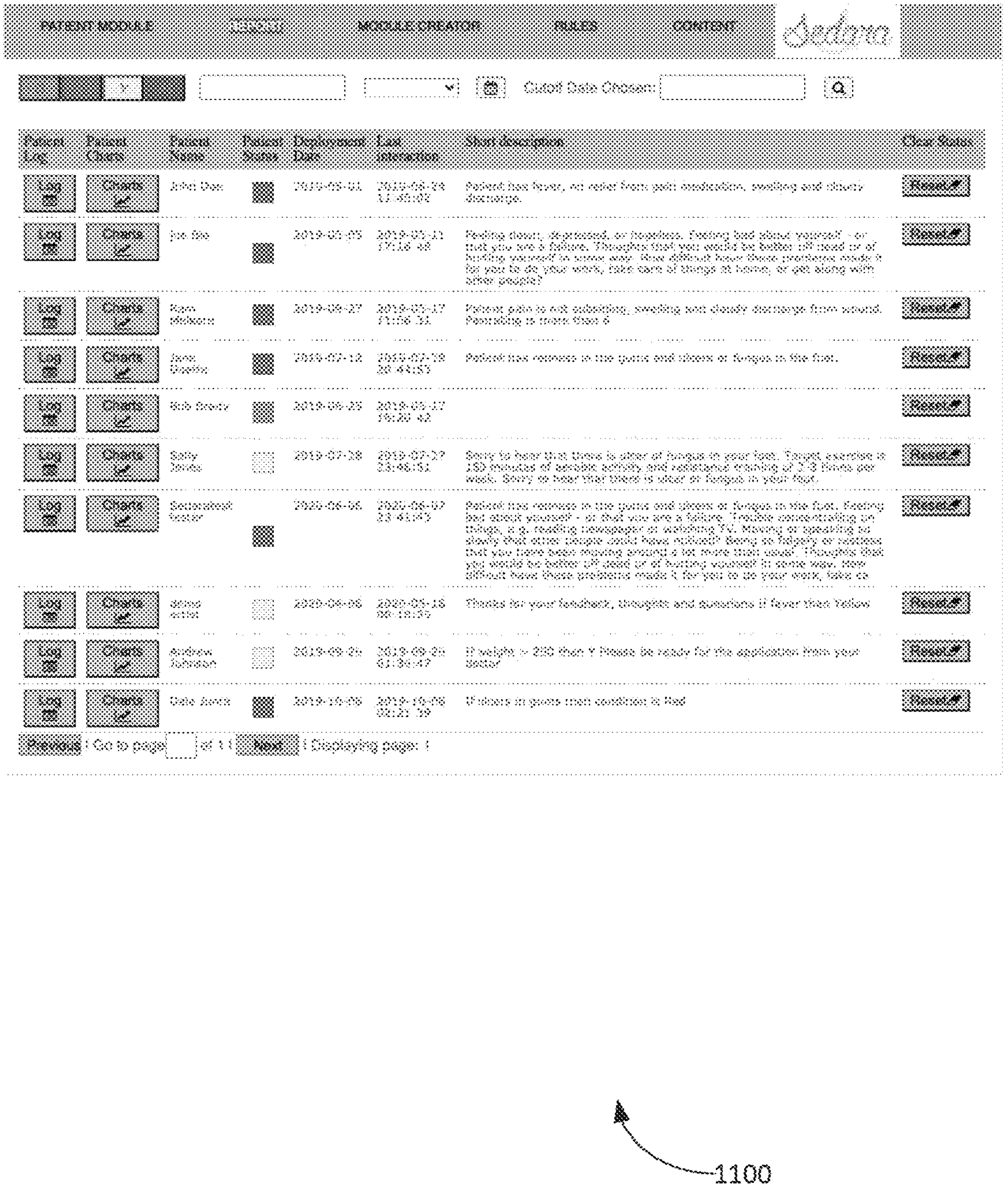
Figure 12:
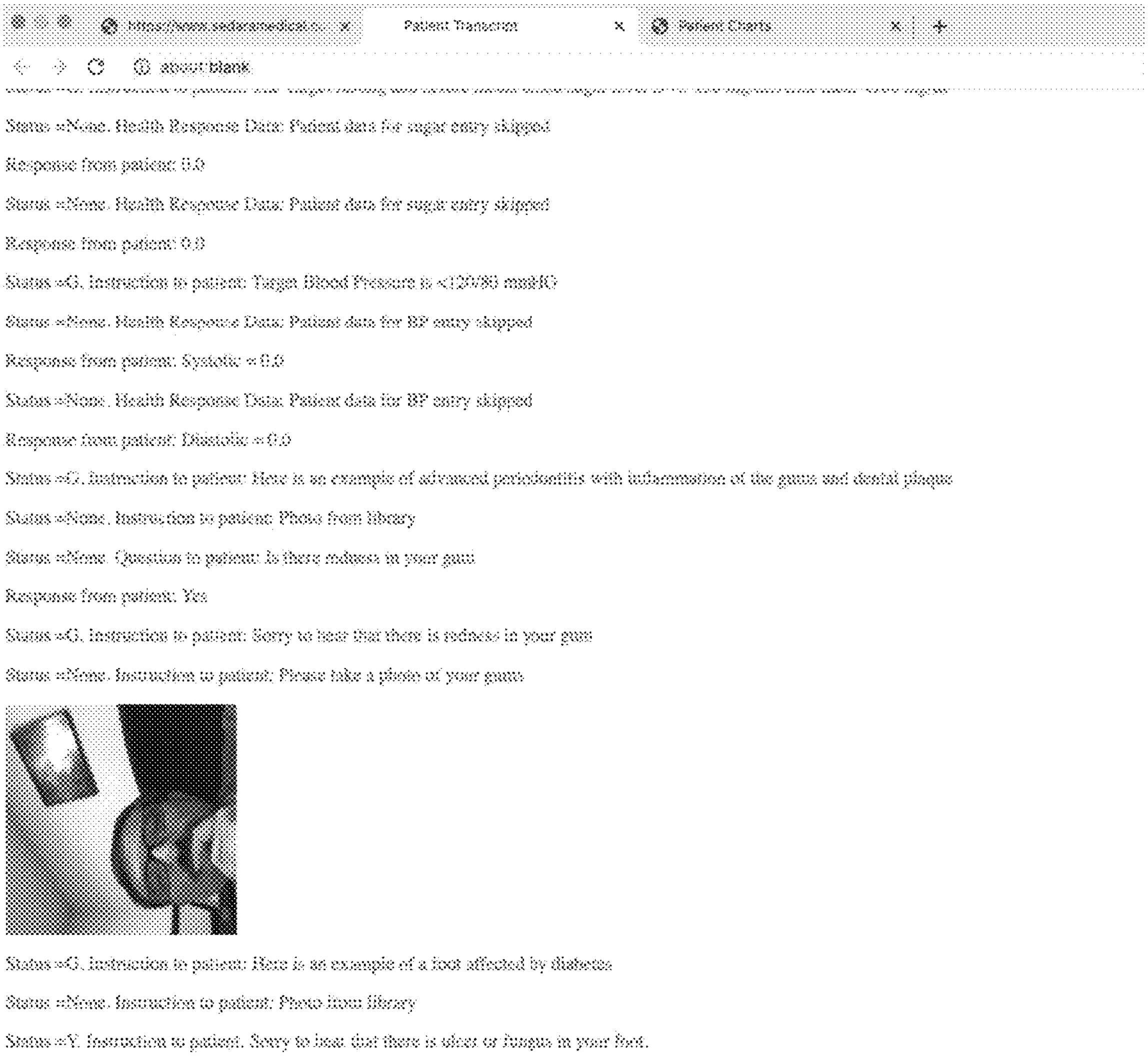
Figure 13:
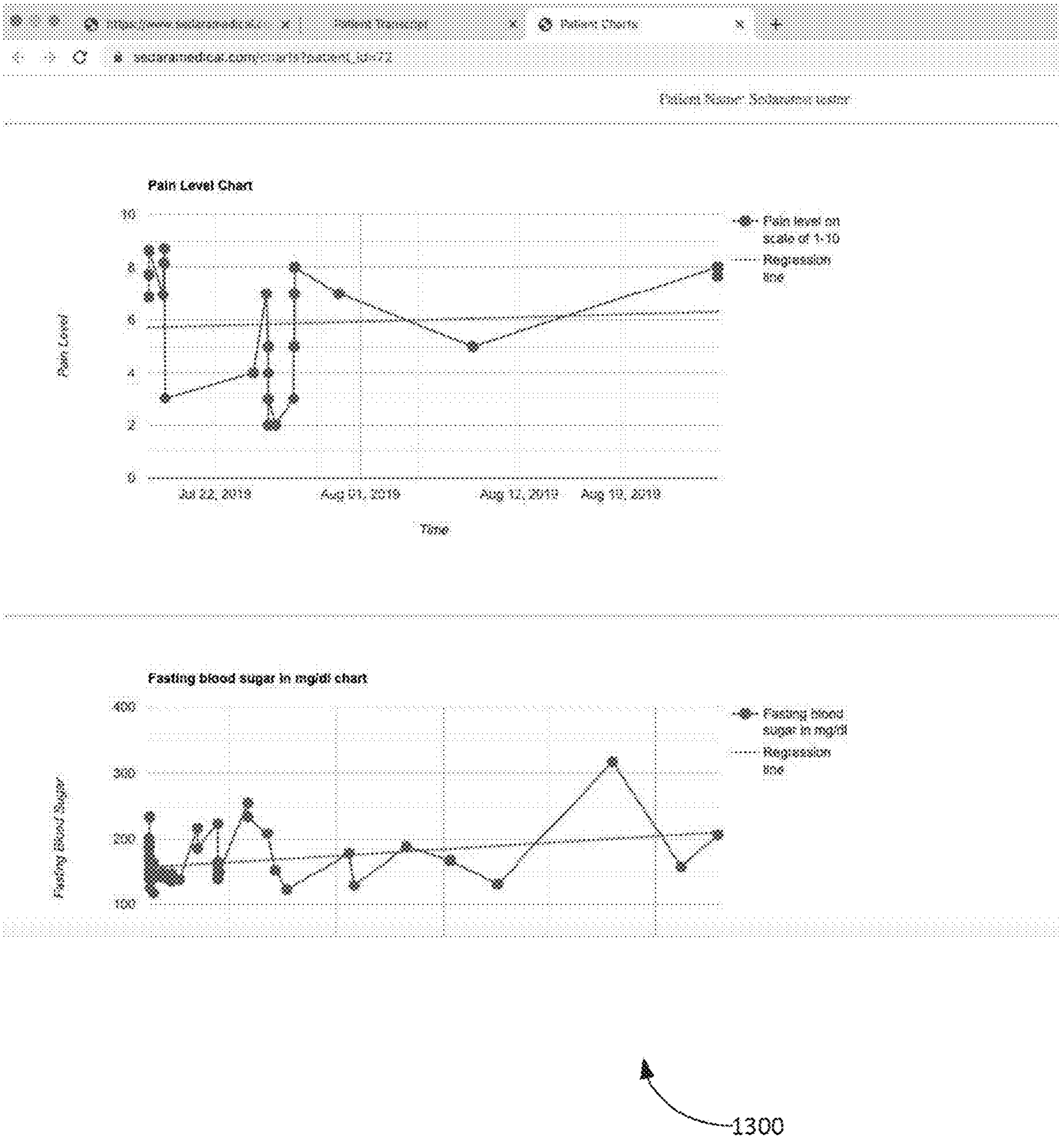

In step 108, process 100 provides reports. The reports can be detailed and summary reports that flag RYG conditions of patients with alerts sent out to care team. For each patient, the RYG status of the patient and a short description of why the status is R, Y or G is displayed as shown in FIG. 11. As shown, clicking the log icon in FIG. 11, displays a complete chronological transcript of the interactions for the patient as shown in FIG. 12. All interactions, data, and photos from the patient are displayed in the transcript. Clicking the charts icon in FIG. 11, displays a chart of all data for the patient as shown FIG. 13.

Figure 14:
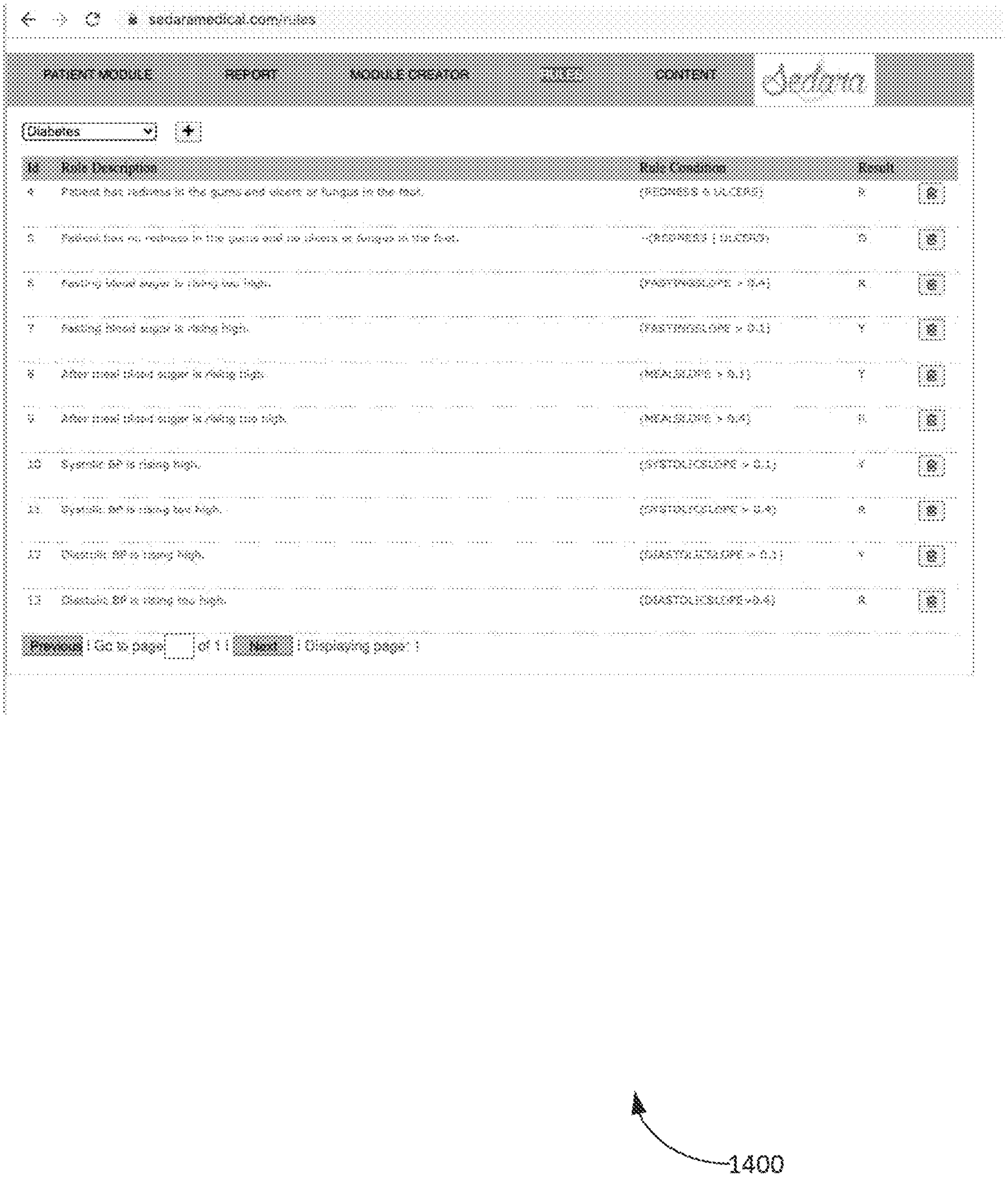
Figure 15:
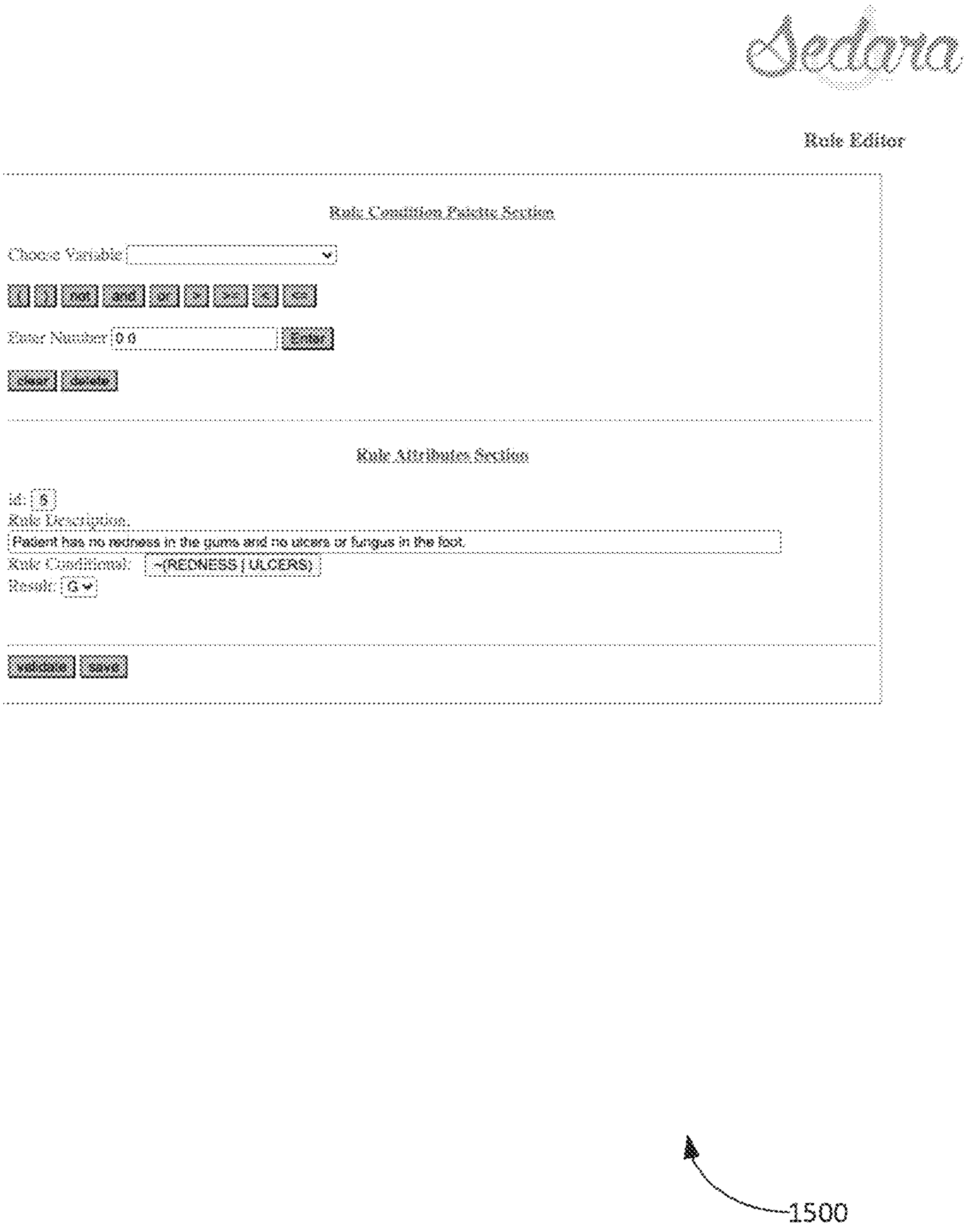

In step 110, process 100 can implement expert system rules and machine learning steps. Data is in from patients in multiple ways including, inter alia:

The applications are fully native with complete access to Bluetooth Devices (e.g. BP, weight, weight, blood sugar, heart rate etc.), wherein applicable data from these devices are brought into our servers;

Automatically obtain health info from Apple Healthkit & Google Fit of the patient;

Manually solicit data from the patients, wherein process 100 creates expert system rules with the help of the doctor that run on the data brought in from the patients as displayed in FIG. 14. These rules stratify a patient's status.

Examples of rules for the surgery follow up application are, inter alia:

Criteria (data tags) FEVER PAINMED (Need stronger med for pain) SWELLING (Wound selling) DISCHARGE (Cloudy or white discharge from the incision);

If FEVER, PAINMED, SWELLING, DISCHARGE then patientstatus="RED";

If not (FEVER or PAINMED or SWELLING or DISCHARGE) then patientstatus="GREEN"; and Else patientstatus="YELLOW"

4. Rules can be created with the UI shown in FIG. 15 in a matter of minutes.

The rules of any complexity can be created by, inter alia:

First selecting the data tags used;

Combining them with logic and arithmetic operations; and applying the risk stratification of the patient as the result if the rule passed.

Figure 16:
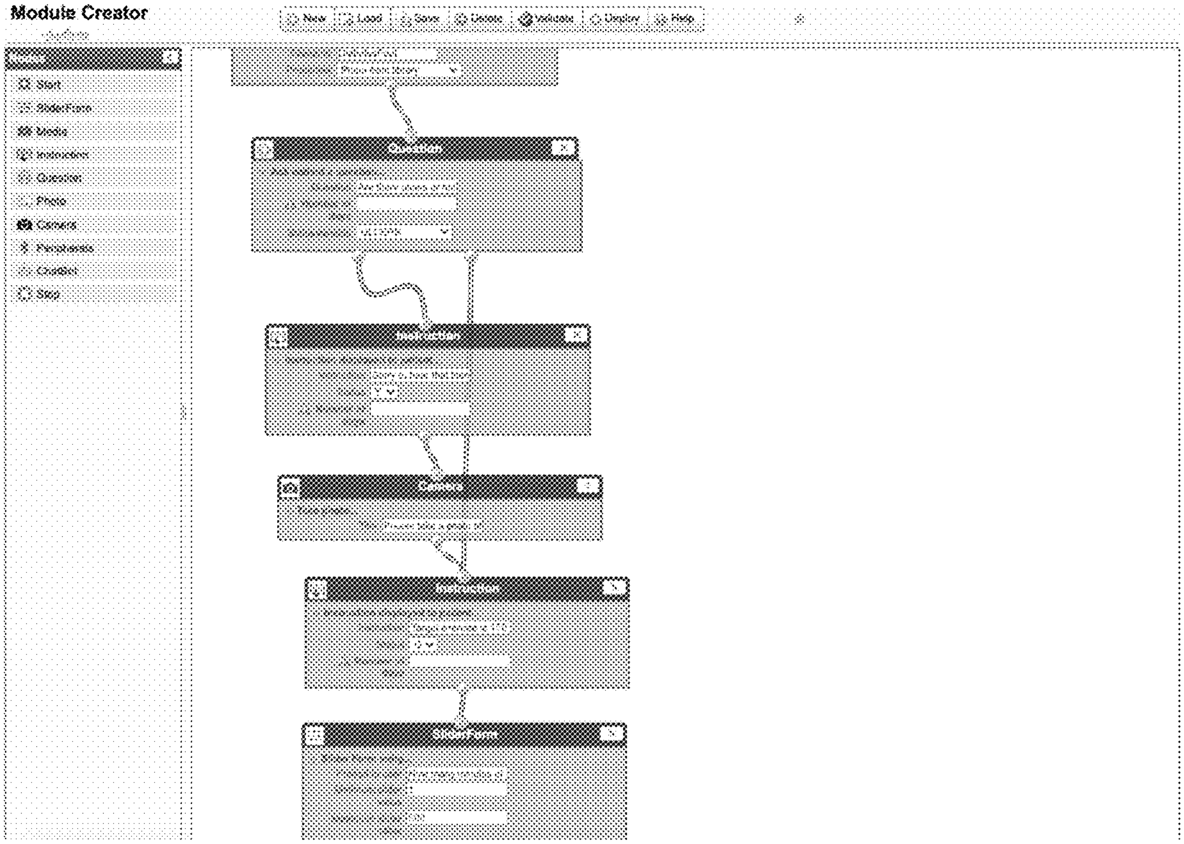

The rule can also be compiled and validated in the UI. In addition, during the creation of the application in the modeler, status of the patient can be designated. As shown in FIG. 16, if the patient replies yes to the question "Are there ulcers or fungus in the foot", then the patient status is turned "Y" as a cautionary step. Process 100 can also have statistical regression run on the data brought in from patients. The rules that govern the statistical regression are created with the doctors' consent. Example of rules that govern the fasting blood sugar regression line is: If slope fastingbloodsugar_line>0.2 then patientstatus="YELLOW" If slope fastingbloodsugar_line>0.4 then patientstatus="RED".

Process 100 can run four schemes in parallel, inter alia:

Expert system rules

Statistical regression rules;

Decision trees;

Machine learning algorithms.

Predictions obtained from the expert system rules, regression, and decision trees are well interpretable and explained. The doctors can govern the rules created. When the predictions from the machine learning model coincide with the former, then there is immediate explainability.

To deal with the situations when the machine learning model predictions are different from the former, process 100 can present the following to the doctors and the care team, inter alia:

Predictions from the expert system rules with a full transcript of the rules that fired;

Predictions from the Statistical regression with a full transcript of the rules that fired;

Predictions from the decision tree with a report that shows the path followed along the tree to reach the decision; and Predictions from the machine learning system with the reports that cite the training data that are closest to the input data and that most influenced the prediction.

To explain the neural network, process 100 can use various methods like Gradient-based explanation and Omission, among others. Process 100 can use a gradient based explanation that uses the partial derivative of the output to the each given input. The higher the metric the higher the relevance of the particular input to the output.

Process 100 can use an omission method by deleting the input and measure the delta change in the output that process 100 can calibrate the relevance of the input. The higher the delta the higher the relevance.

In one example, the following are the Al algorithms can be used by process 100. Standard neural network that has a large number of processor nodes. These nodes carry out parallel operations and are organized into tiers. Input is provided to the first tier. Input progresses from each tier after processing, as output to the successive tier. The last tier sends out the output to the user. Each tier is made up smaller nodes. The nodes in the sandwiched tier are connected to the nodes in the tier before and the nodes in the tier after. Knowledge is disseminated into the network with rules that are programmed by us and with rules that the network learns by back propagation. Each node has weights that signify the importance of the input fed to it. The weights are configured during the learning process to favor the inputs that contribute most to the correct output. A convolutional neural network introduces one or more convolutional layer. These layers can be configured as completely interconnected or configure in a pooled manner. Before passing the result to the next layer, the convolutional layer uses a convolutional operation on the input. Process 100 can use the convolutional neural network for natural language processing, semantic parsing, and paraphrase detection. Decision trees can be used for patient status classification. The algorithms can be trained by training data points. Using the training data, the decision trees recursively partition the feature space and assign a label to each partition. The model tree is then used to predict the classification of future input points. The main advantage of decision trees is that they are very interpretable. Natural language processing algorithms will be used to parse and interpret doctor notes and patient queries. This is needed as this kind of data is unstructured. Process 100 can incorporate the following algorithms on the unstructured data. These algorithms will be trained to find relevant words in the unstructured text.

Process 100 can implement named entity recognition models: search for specific keywords (names) and then proceed to categorize them into predefined groups. Process 100 can use entity resolution models. Process 100 can find multiple records that belong to the same entity and merge them into one record. Example records that belong to an entity are diagnosis, symptoms, protocols, procedure, and drug codes.

In a chatbot for patients example, process 100 can, for a given a question, phrase from the user find the answer for the question from the database of knowledge. Fundamentally, given two texts, find a universal similarity metric that can be used to determine whether the two have similar meaning.

In one example, the following are the steps process 100 can incorporate the following steps, inter alia:

Data Preprocessing that can include: Dropping Punctuation; Drop Stop Words (e.g. stop words taken from the NLTK stop words 'English' dictionary ('I', 'Me', 'Me', 'Ours')-->Words that do not contribute to the informational part of the question. Stemming can be used. For example, Porter stemming (conservative, retains more information); etc. can be utilized. Porter to retain more information possible. Process 100 can use feature engineering. This can extract metrics to deduce the similarity of two pieces of text. Example, similarity metrics can include, inter alia: Jaccard Similarity that is defined as the size of intersection divided by the size of the union of the two sets.

Process 100 can use Cosine Similarity. This can be a measure of the similarity between two vectors that measures the cosine of the angle between them.

Process 100 can train the model. For example, process 100 use the k-fold cross-validation method, among others. Process 100 can divide the complete dataset into k disjoint subsets of same size. Process 100 can then train the model on k−1 subsets and test on the leftover subset. Process 100 can repeat the above process k times, swapping the test subset for a training set. The average of the k test errors will give us the test error. This scheme can ensure that every row of data is used equally often for training and once for testing. The bias in the data is reduced. The testing data would cover a diverse case mix. Next, process 100 can avoid underfitting and overfitting. The model is underfitting if there are two symptoms:

If testing error<training error.

If the whole model accuracy is low. Underfitting is caused by dropout: the acts of randomly setting activations to zero to avoid overfitting. Dropouts have to be prudently managed, to avoid over or underfitting. Dropouts have to added in manageable quantities to the first layer.

Following are the steps to reduce underfitting:

Increasing the number of parameters in ML model;

Increasing the complexity of the model;

Increasing the time for training till the ML's cost function is minimized.

Overfitting happens when the model fits the training data too well that it becomes too specific to the training data and loses generality. The accuracy on the testing data or for that matter any data is not desired. Following are the steps to reduce overfitting:

Add as much valid data as possible.

Use data augmentation: as an example, claims data might miss information such as how the patient followed the treatment.

Process 100 can use techniques that can approximate the missing information from combining existing information. Process 100 can add regularization, dropout, and L1/L2 regularization. Following is all the input data that process 100 can consume to train various machine learning algorithms well and make predictions at run time in the best manner, inter alia:

EHR records;

Inpatient claims;

Outpatient claims;

Carrier claims;

- Prescription Drug transactions;
- Diagnosis•Treatments;
- lab results;
- Doctor notes;
- Quality of care provided;
- Information from specialist visit;
- social determinants of health (SDoH) data (e.g. socioeconomic status, rural/urban; food intake quality; education; Living conditions; etc.).

Example Computing Systems

FIG. 17 depicts an exemplary computing system 1700 that can be configured to perform any one of the processes provided herein. In this context, computing system 1700 may include, for example, a processor, memory, storage, and I/O devices (e.g., monitor, keyboard, disk drive, Internet connection, etc.). However, computing system 1700 may include circuitry or other specialized hardware for carrying out some or all aspects of the processes. In some operational settings, computing system 1700 may be configured as a system that includes one or more units, each of which is configured to carry out some aspects of the processes either in software, hardware, or some combination thereof.

FIG. 17 depicts computing system 1700 with a number of components that may be used to perform any of the processes described herein. The main system 1702 includes a motherboard 1704 having an I/O section 1706, one or more central processing units (CPU) 1708, and a memory section 1710, which may have a flash memory card 1712 related to it. The I/O section 1706 can be connected to a display 1714, a keyboard and/or other user input (not shown), a disk storage unit 1716, and a media drive unit 1718. The media drive unit 1718 can read/write a computer-readable medium 1720, which can contain programs 1722 and/or data. Computing system 1700 can include a web browser. Moreover, it is noted that computing system 1700 can be configured to include additional systems in order to fulfill various functionalities. In another example, computing system 1700 can be configured as a mobile device and include such systems as may be typically included in a mobile device such as GPS systems, gyroscope, accelerometers, cameras, etc.

Additional Systems

FIG. 18 illustrates an example system 1800 for generating, delivering, and displaying cross platform personalized digital software applications, according to some embodiments. System 1800 can include machine-learning engine 1802. Machine-learning engine 1802 can implement the various ML/AI functionalities provided herein. ML engine 1802 can leverage various ML methods to implement the processes and systems of FIGS. 1-16 discussed supra. ML engine 1802 can use exemplary hardware environment 1900 in some examples.

FIG. 18 illustrates an example system 1800 for generating, delivering, and displaying cross platform personalized digital software applications, according to some embodiments. FIG. 19 illustrates a schematic representation of an exemplary hardware environment 1900 for generation of datasets for machine learning models used to determine a personalized digital software application, according to some embodiments. The hardware environment 1900 includes a first compute node 1910 that is employed to build a dataset (e.g. an application definition file(s) dataset, electronic health records dataset, expert system rules data, user profile data, etc.) for later use by machine-learning systems. In various embodiments the compute node 1910 is a server but can be any computing device with sufficient computing capacity such as a server, personal computer, or smart phone. The compute node 1910 stores the dataset to a database 1920. Database 1920 can also store data obtained from the care team as they ask questions and interact with the patient (e.g. see supra) as well as data obtained from various peripheral devices. For example, peripheral devices can include data that is obtained from peripheral devices that are connected to the mobile phone via protocols like Bluetooth etc. (e.g. heartrate, BP, blood sugar, weight, temperature etc.).

More specifically, first compute node 1910 builds a data set from various example sources, including, inter alia: United States Census Bureau server(s), American Community Survey ACS server(s), National Institutes of Health server(s), Center for Disease Control server(s), Bureau of Labor Statistics server(s), Department of Transportation server(s), server(s) associated with data including Risk Surveys National Centers for Environmental Information National Center for Health Statistics—Mortality Files U.S. Congress, Joint Economic Committee, Social Capital Project. "The Geography of Social Capital in America.", County Health Rankings, server(s) associated with data including, server(s) associated with data including the Behavioral Risk Factor Surveillance System County Business Patterns FRED database Federal Reserve Data.gov Economic Research Service, U.S. department of agriculture server(s), Federal Interagency Forum on Aging-Related Statistics server(s), Public Use Microdata Samples (PUMS) server(s), Environmental Protection Agency server(s), electronic medical records databases, the MEDLINE database, the patient's own medical records (e.g. from a set of digital EMR records for the patient, etc. As noted supra, this data can also include, inter alia, any data sources for: patient EHR records; inpatient claims; outpatient claims; carrier claims; prescription drug transactions; patient diagnosis; patient treatments; patient lab results; digitized doctor notes; quality of care provided; Information from specialist visit; social determinants of health (SDoH) data (e.g. socioeconomic status, rural/urban; food intake quality; education; living conditions; etc.). This data is stored in database 1920.

First compute node 1910 can use acquired data to provide values for specified feature variables. Accordingly, first compute node 1910 can include web scrappers, content analytics and summarization functionalities, NLP engines, computer-vision engines, mobile application builders, etc.

A second compute node 1930, which can be the same compute node as first compute node 1910, in some embodiments, accesses the database 1920 in order to utilize the dataset to train deep learning models to produced trained model files 1940. The second compute node 1930 can optionally also validate deep learning models.

A user employing a third compute node 1950 can upload an image or video or care team feedback, including a target therein, to an application server 1960 across a network like the Internet 1970, where the application server 1960 hosts a machine-learning engine, an application definition file engine, and a patient risk engine (e.g. see infra). Machine-learning engine and application definition file engine manage the generation of machine learning models used to generate and optimize an application definition file for the patient. Based on the patient's inputs into the series of nodes in an application created by the optimized application definition file, the machine-learning engine, and patient risk engine manage and optimize a risk score assignment to the patient.

In response to a request from the compute node 1950, such as a mobile phone or PC, to generate and optimize an application definition file and/or calculate a patient risk score, the application server 1960 connects the third compute node 1950 to a fourth compute node 1980, which can be the same compute node as either the first or second compute nodes 1910, 1930, in some embodiment. Compute node 1980 uses the model files 1940 to infer answers to the queries posed by the compute node 1950 (e.g. via a personalized mobile device application that asks a series of questions/requests based on the nodes included in an application definition file, etc.) and transmits the answers back through the application server 1960 to the compute node 1950. Application server 1960 uses one or more deep learning methods to generate and validate a patient/user model and using the patient's input into the application builder and using an application modeler creates a personalized digital software applications. The personalized digital software applications can then be electronically communicated to the patient's clinic (along with the other relevant input data) for analysis (e.g. using compute node 1950, etc.).

Compute node 1980 can use machine learning to infer answers and components of the application optimization thereof. Example machine learning techniques that can be used herein include, inter alia: decision tree learning, association rule learning, artificial neural networks, inductive logic programming, support vector machines, clustering, Bayesian networks, reinforcement learning, representation learning, similarity, and metric learning, and/or sparse dictionary learning. Random forests (RF) (e.g. random decision forests) are an ensemble learning method for classification, regression, and other tasks, that operate by constructing a multitude of decision trees at training time and outputting the class that is the mode of the classes (e.g. classification) or mean prediction (e.g. regression) of the individual trees. RFs can correct for decision trees' habit of overfitting to their training set. Deep learning is a family of machine learning methods based on learning data representations. Learning can be supervised, semi-supervised or unsupervised.

Machine learning can be used to study and construct algorithms that can learn from and make predictions on data. These algorithms can work by making data-driven predictions or decisions, through building a mathematical model from input data. The data used to build the final model usually comes from multiple datasets. In particular, three data sets are commonly used in different stages of the creation of the model. The model is initially fit on a training dataset, that is a set of examples used to fit the parameters (e.g. weights of connections between neurons in artificial neural networks) of the model. The model (e.g. a neural net or a naive Bayes classifier) is trained on the training dataset using a supervised learning method (e.g. gradient descent or stochastic gradient descent). In practice, the training dataset often consist of pairs of an input vector (or scalar) and the corresponding output vector (or scalar), which is commonly denoted as the target (or label). The current model is run with the training dataset and produces a result, which is then compared with the target, for each input vector in the training dataset. Based on the result of the comparison and the specific learning algorithm being used, the parameters of the model are adjusted. The model fitting can include both variable selection and parameter estimation. Successively, the fitted model is used to predict the responses for the observations in a second dataset called the validation dataset. The validation dataset provides an unbiased evaluation of a model fit on the training dataset while tuning the model's hyperparameters (e.g. the number of hidden units in a neural network). Validation datasets can be used for regularization by early stopping: stop training when the error on the validation dataset increases, as this is a sign of overfitting to the training dataset. Finally, the test dataset is a dataset used to provide an unbiased evaluation of a final model fit on the training dataset. If the data in the test dataset has never been used in training (e.g. in cross-validation), the test dataset is also called a holdout dataset.

Returning to system 1800, system 1800 can include mobile device application generation engine 1804. Mobile device application generation engine 1804 can customize and deploy built application modules to Android/iPhones for Patients and caregivers. Mobile device application generation engine 1804 can deploy fully native application with complete access to Bluetooth Devices (BP, weight etc.). Mobile device application generation engine 1804 can enable native android/iPhone applications run the application module that takes the patient through the regimen. Mobile device application generation engine 1804 can create educational content for patients. Mobile device application generation engine 1804 can enable same native application deployed to Android/iPhone/iPad instantly (e.g. assuming processing latency, networking latency, etc.) with consistent experience; Mobile device application generation engine 1804 can provide the instructions in the application definition file could be modified based on patient feedback. Mobile device application generation engine 1804 can generate the application definition file on a patient device can be updated by sending a SMS message or push notification to the device. Mobile device application generation engine 1804 can handle/manage application deployment to an application store. Mobile device application generation engine 1804 can obtain records of patient interactions from process 100.

System 1800 can include application definition file engine 1806. Application definition file engine 1806 can create the application definition file with a drag and drop application modeler; interface with chatbot, modeler creates the application definition file that when runs on the mobile phone of the patient can follow the protocol and logic created in the application by the care team, includes application modeler (e.g. as discussed in FIG. 1, etc. supra).

System 1800 can include patient risk engine 1808. Patient risk engine 1808 can determine patient risk and generate patient risk scores. Patient risk engine 1808 can generate and manage models that capture relationships among many factors to allow assessment of risk or potential associated with a particular set of conditions, guiding decision-making for candidate transactions. Patient risk engine 1808 can generate various detailed and summary reports that flag patient risk stratification (e.g. RYG, etc.) conditions of patients with alerts sent out to care team. Patient risk engine 1808 can apply risk stratification of the patient as the result if the rule passed.

System 1800 can include API(s) 1810. API(s) 1810 can enable the application, integrated chat bots, etc. to communicate with third-party systems. For example, the application can communicate with care giver computing systems, data sources, etc.

System 1800 can include data acquisition engine 1812. Data acquisition engine 1812 can obtain data related to the user/patient state. For example, data acquisition engine 1812 can obtain data for data store 1920 and data used by first compute node 1910, etc. Data can be obtained based on specified triggers and/or on a periodic basis.

Conclusion

Although the present embodiments have been described with reference to specific example embodiments, various modifications and changes can be made to these embodiments without departing from the broader spirit and scope of the various embodiments. For example, the various devices, modules, etc. described herein can be enabled and operated using hardware circuitry, firmware, software or any combination of hardware, firmware, and software (e.g., embodied in a machine-readable medium).

In addition, it will be appreciated that the various operations, processes, and methods disclosed herein can be embodied in a machine-readable medium and/or a machine accessible medium compatible with a data processing system (e.g., a computer system), and can be performed in any order (e.g., including using means for achieving the various operations). Accordingly, the specification and drawings are to be regarded in an illustrative rather than a restrictive sense. In some embodiments, the machine-readable medium can be a non-transitory form of machine-readable medium.

What is claimed is:

1. A computerized method for generating a personalized digital software application comprising:

with an application design system running on a specific operating system:

providing an application modeler engine;

with the application modeler engine:

providing a graphical display of a palate that comprises a list all the nodes that are available to include in an application definition file, receiving a set of nodes via a drag and drop operation into the application definition file, wherein the set of nodes are wired together by the drag and drop operation to generate a graph that is saved as the application definition file, and wherein each node comprises a plurality customizable parameters to tailor an information for an application, defining and integrating a chatbot into the personalized digital software application, wherein the chatbot receives a query from the user, wherein the chatbot comprises a natural language processing engine that is configured to analyze the query, and replies with a multi-media answer to the mobile device, wherein the multi-media answer comprises an image-based information for the query or a video-based information for the query to be displayed on the mobile device, automatically creating the application definition file to run on the mobile device of a user, wherein the application definition file follows a protocol and logic created in the application by a care team and the drag and dropped nodes; and with a machine-learning engine:

generating a plurality of machine learning models configured to generate and optimize the application definition file for the user, wherein one or more deep machine learning methods are configured to generate and validate the user and use the user's input to create the application as a personalized digital software application, wherein the one or more deep machine learning methods comprise:

a machine learning pipeline configured to analyze user data to determine risk stratification, wherein the deep machine learning methods implement statistical regression on the data from users to determine temporal patterns, wherein regression slopes for clinical measurements are calculated and compared to predefined thresholds to determine user status, wherein if a slope of a clinical measurement exceeds a first threshold then a user status is assigned a first risk level, and if the slope exceeds a second higher threshold then the user status is assigned a second higher risk level, wherein the plurality of machine learning models comprise:

a first machine learning model trained to process user-specific data from the set of nodes, a second machine learning model configured to optimize the application definition file based on the user inputs, a third machine learning model configured to infer answers and components for the application, and wherein the plurality of machine learning models are trained using a dataset comprising measurements from a peripheral, the user input via a status variable, an answer to a question, and a medical record;

with the plurality of machine learning models with the application definition file as an input, generating an optimized application definition file for the user, with the optimized application definition file, generating the application from the optimized application definition file, wherein the plurality of machine learning models are configured to use machine learning to infer a plurality of answers and components of the application, deploying the application to a user's mobile device, and receiving a set of user inputs into the set of nodes;

based on the user's inputs into the set of nodes, optimize a risk score assignment to the user; and displaying the image-based information for the query or the video-based information for the query that is displayed on the mobile device;

providing the application deployed to the user's mobile device, wherein each node in the application definition file is executed in a native mode on the native application run on the user mobile device with a complete access to a plurality of peripheral wireless devices, and wherein multiple applications are deployed to the user's mobile device and run as a single application in the user's mobile device, wherein the application definition file created by the modeler is run as a native application deployed to the mobile device with a consistent experience.

2. The computerized method of claim 1, wherein the list of all the nodes that are available comprises a node that defines a start point of the application.

3. The computerized method of claim 2, wherein the list of all the nodes that are available comprises a node that defines a slider form for providing a data input in a range of pain rating from 1 to 10.

4. The computerized method of claim 3, wherein the list of all the nodes that are available comprises a node that defines an instruction for displaying a set of instructions to the user for inputting data into the application.

5. The computerized method of claim 4, wherein the list of all the nodes that are available comprises a node that defines a digital media for displaying an audio and a video content locally from a mobile phone or via the Internet.

6. The computerized method of claim 5, wherein the list of all the nodes that are available comprises a node that defines a question to the user for asking a set of Yes/No questions to the user for soliciting additional input from the user.

7. The computerized method of claim 6, wherein the list of all the nodes that are available comprises a node that defines an application functionality for displaying a set of digital photos to the user.

8. The computerized method of claim 7, wherein the list of all the nodes that are available comprises a node that defines an application functionality for enabling the patient take a digital photograph of a patient injury.

9. The computerized method of claim 8, wherein the list of all the nodes that are available comprises a node that defines the application definition file.

10. The computerized method of claim 9, wherein the list of all the nodes that are available comprises a node that defines where an execution of the personalized digital software application begins, as user navigates through the personalized digital software application until a stop point of the patient user navigation.

11. The computerized method of claim 1, wherein the drag and drop operation is performed by a user.

12. The computerized method of claim 1, wherein each node comprises a set of customizable parameters used for tailoring the personalized digital software application.

13. The computerized method of claim 1, wherein the deployed application enables a communication session between a care team and the user via an electronic messaging format.

14. The computerized method of claim 13, wherein the application displays digital photographs that comprise one or more generic educational photographs or a set of digital photographs specific to a user state.

* * * * *